United States Patent
Kleppe et al.

(10) Patent No.: US 9,588,045 B2
(45) Date of Patent: Mar. 7, 2017

(54) METHOD FOR GENERATING A MICROSCOPE IMAGE AND MICROSCOPE

(75) Inventors: Ingo Kleppe, Jena (DE); Yauheni Novikau, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 451 days.

(21) Appl. No.: 13/499,328

(22) Filed: Mar. 30, 2012

(65) Prior Publication Data

US 2013/0068967 A1 Mar. 21, 2013

(30) Foreign Application Priority Data

Sep. 30, 2009 (DE) .................. 10 2009 043 747

(51) Int. Cl.
| | |
|---|---|
| *G02B 21/06* | (2006.01) |
| *G01N 21/64* | (2006.01) |
| *G02B 21/36* | (2006.01) |
| *G02B 27/56* | (2006.01) |
| *G02B 27/58* | (2006.01) |
| *H01L 27/146* | (2006.01) |

(52) U.S. Cl.
CPC ......... *G01N 21/64* (2013.01); *G01N 21/6458* (2013.01); *G02B 21/06* (2013.01); *G02B 21/367* (2013.01); *G02B 27/56* (2013.01); *G02B 27/58* (2013.01); *H01L 27/146* (2013.01)

(58) Field of Classification Search
CPC ........................... G01N 21/64; G01N 21/6458
See application file for complete search history.

(56) References Cited

U.S. PATENT DOCUMENTS

| | | | |
|---|---|---|---|
| 5,867,604 A | 2/1999 | Ben-Levy et al. | |
| 6,255,642 B1 | 7/2001 | Cragg et al. | |
| 2005/0174631 A1 | 8/2005 | Nishiwaki et al. | |
| 2007/0023686 A1 | 2/2007 | Wolleschensky et al. | |
| 2008/0088920 A1 | 4/2008 | Wolleschensky | |
| 2009/0318815 A1* | 12/2009 | Barnes et al. ................ | 600/473 |
| 2010/0135547 A1* | 6/2010 | Lee et al. ...................... | 382/128 |

(Continued)

FOREIGN PATENT DOCUMENTS

| | | |
|---|---|---|
| DE | 197 02 753 A1 | 7/1998 |
| DE | 10 2004 034998 A1 | 2/2006 |

(Continued)

OTHER PUBLICATIONS

English translation of International Preliminary Report on Patentability & Written Opinion of the International Searching Authority (Forms PCT/IB/373 and PCT/ISA/237).

(Continued)

*Primary Examiner* — Yara B Green
(74) *Attorney, Agent, or Firm* — Duane Morris LLP

(57) ABSTRACT

The invention relates to a method and a microscope for generating a microscopic image, wherein a) the sample is illuminated in each case by the microscope lens using the TIRF method; and b) the sample is illuminated in a structured fashion in different displacement positions of the structure. The sample light of the method according to a) and b) is detected in each case for generating an image of at least once sample region, wherein the sample images generated according to a) and b) are set off against one another, preferably multiplied, and the result is stored for generating a new sample image.

9 Claims, 5 Drawing Sheets

(56) References Cited

U.S. PATENT DOCUMENTS

2013/0068967 A1 3/2013 Kleppe et al.

FOREIGN PATENT DOCUMENTS

| DE | 10 2008 009 216 A1 | 8/2009 |
|----|---|---|
| EP | 1 157 297 B1 | 11/2002 |
| EP | 1 741 485 A1 | 3/2005 |
| JP | 2008-542826 | 11/2008 |
| WO | WO 2006/127692 A2 | 11/2006 |
| WO | WO 2008/129233 A1 | 10/2008 |

OTHER PUBLICATIONS von Gustafson, et al.; "Doubling the lateral resolution of wide field fluorescence microscopy"; SPIE 2000; 3919:141-150.

* cited by examiner

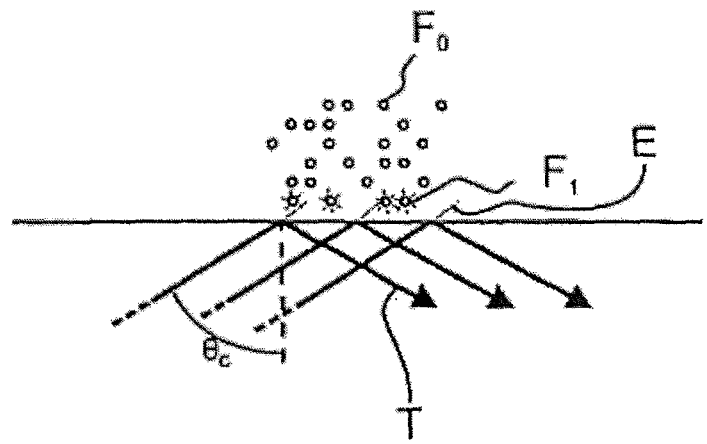
Figure 1 - State of the Art
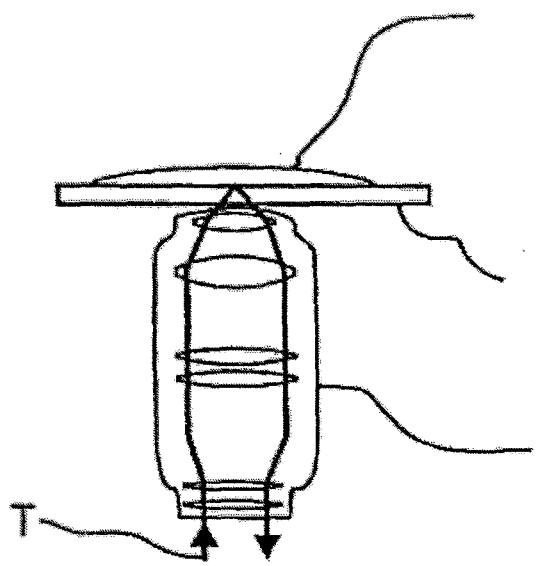
Figure 2 - State of the Art

Fig. 3
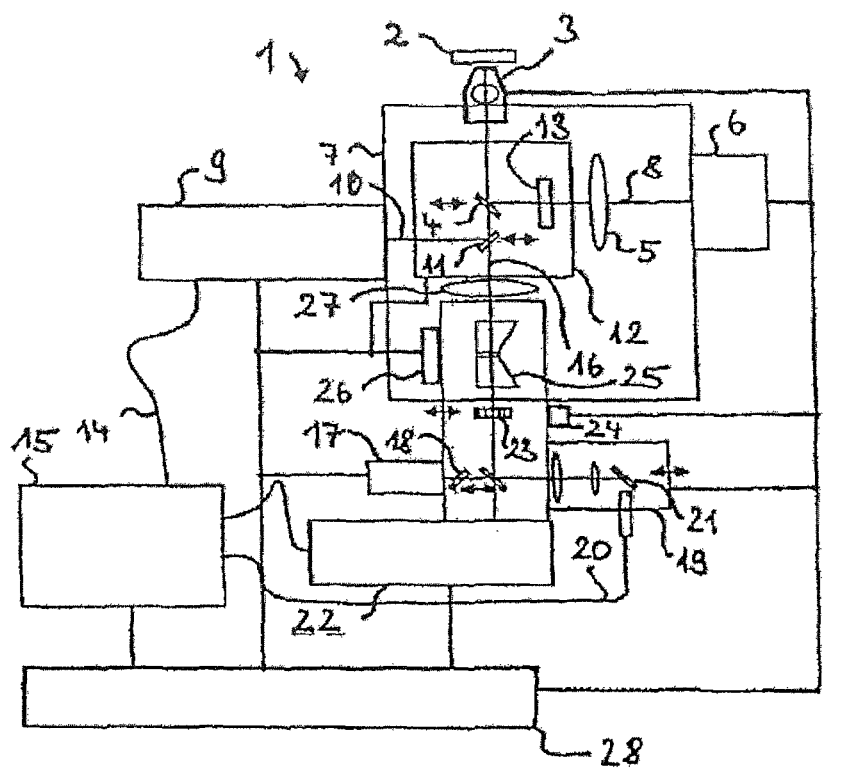
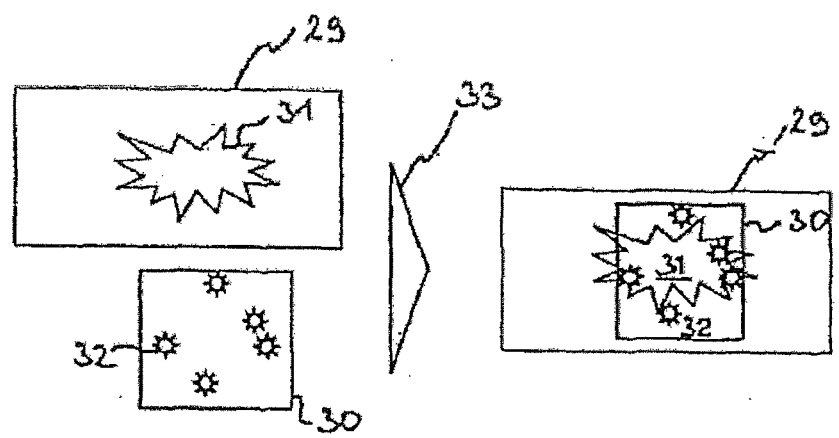
Fig. 4

METHOD FOR GENERATING A MICROSCOPE IMAGE AND MICROSCOPE

RELATED APPLICATIONS

The present application is a U.S. National Stage application of International PCT Application No. PCT/EP2010/005295 filed on Aug. 28, 2010 which claims priority benefit of German Application No. DE 10 2009 043 747.9 filed on Sep. 30, 2009, the contents of each are incorporated by reference in their entirety.

BACKGROUND OF THE INVENTION

Microscopy with application of the so-called total internal reflection fluorescence (TIRF) is a special form of fluorescence microscopy. It is, for example, disclosed in WO 2006/127692 A2 (for example, in FIGS. 9 and 10C). FIG. 1 clarifies the context. The fluorophores $F_0$ of the specimen P are excited to fluoresce $F_1$ by means of an evanescent illumination field E solely in a thin layer behind the interface between the cover glass D and the specimen. The evanescent illumination field E is generated in the specimen, in which the excitation radiation T inside the cover glass D is conducted at an angle $\theta_c$, which leads to total internal reflection, onto the interface between the cover glass and the specimen. Since only the thin layer is excited to fluoresce, it is possible to attain a very high axial resolution. The optical axial resolution of a TIRF microscope results from the penetration depth d of the evanescent field in the specimen. Depending on the angle of incidence θ, the axial solution is the product of $$d=\lambda/[4\pi\sqrt{(n_1^2 \sin^2 \theta - n_2^2)}],$$

where λ is the excitation wavelength, $n_1$ is the index of refraction of the cover glass, and $n_2$ is the index of refraction of the specimen medium.

Usually the illumination passes, as shown in FIG. 2 in schematic form, through the microscope objective lens O into its edge region in such a way that on leaving the objective lens O the illumination light crosses the optical axis of the objective lens O at an angle that is greater than or equal to the angle of total internal reflection $\theta_c$. The microscope objective lens O has to possess a high numerical aperture in order to provide the mandatory large angle of incidence required for the excitation light T. The resulting fluorescence is collected through the same objective lens O and projected onto a CCD camera (not illustrated).

Prior Art

Similarly WO 2006/127692 A2 discloses the use of photo activated fluorescence dyes (English: photo activated localization microscopy, PALM, also PAL-M) in order to enhance the resolution capability of the microscope. Very low intensity light having an activation wavelength can transform (activate) an extremely small number of randomly distributed fluorophores into an excitable state; and then these fluorophores can be excited to fluoresce by light having an excitation wavelength in a way known from the prior art. The remaining, unactivated fluorophores cannot be excited to fluoresce by the excitation wavelength. Owing to the random distribution the activated and excited fluorophores are usually arranged spatially so far apart that the intensity distributions of the point source images resulting from the fluorescence events appear in a diffraction limited range without overlapping. This also applies especially to a projection onto a two-dimensional image, in which the intensity distributions automatically extend over a plurality of pixels (English: picture elements; pixels) owing to the diffraction expansion. In the PAL microscopy a plurality of single images are acquired in each instance with a small number of fluorescence events that usually do not overlap spatially. In so doing, the activation of a small group of fluorophores is repeated, only after the last activated fluorophores are bleached. The origins of the individual fluorescence events are localized in the single images by means of a computational balancing with subpixel resolution using the diffraction expanded intensity distributions and are entered into a high resolution target image.

Discloses a method to improve lateral resolution of optical imaging system by scanning the object with periodic pattern illumination.

A high resolution microscopy method within the scope of the invention is addressed, for example, in U.S. Pat. No. 5,867,604, in which an object with periodic structure is scanned.

In EP 1157297 B1 non-linear processes are utilized by means of structured illumination. The saturation of the fluorescence serves as the non-linearity. Owing to a structured illumination, which is generated by means of an illumination radiation modulator, the spatial spectrum of the object is shifted relative to the transfer function of the optical system. Stated more precisely, the spectrum shift means that the spatial frequencies of the object VO are transferred at a spatial frequency VO–Vm, where Vm is the frequency of the structured illumination. At a given spatial frequency that can be maximally transferred by the system, this strategy enables the transfer of spatial frequencies of the object that exceed the maximum frequency of the transfer function by the shift frequency Vm. This approach requires a reconstruction algorithm in order to generate an image and to use a plurality of acquisitions for an image. Thus, EP 1157297 B1, which is incorporated by reference in its entirety into the disclosure herein with respect to the corresponding description of the resolving microscopy method, uses a structured wide field illumination of the specimen, wherein a stripe-shaped modulation is imposed, for example, by means of an amplitude/phase grating. The fluorescence in the specimen is also detected in wide field. At this stage the modulation is moved into at least three different rotational positions, for example 0 deg., 120 deg., and 240 deg.; and in each rotational position the modulation is shifted into at least three different positions. In each shift of the rotational positions (thus, in total at least 9 image positions), the specimen is detected in wide field. Furthermore, the grating has frequencies as close as possible to the limit frequency, which the optical arrangement that is used is capable of transferring. Then the aforementioned spectrum shift occurs with the application of a Fourier analysis, so that, in particular, the 0th and +/−1st diffraction order in the images is evaluated. This microscopy method is also called the SIM [structured image microscopy] method.

Object of the Invention

A further development of the SIM method can be achieved with a line shaped illumination, which lies perpendicular to the stripe direction of the modulation. Then there is a line shaped illumination, wherein the stripe structure recurs along the line. The line shaped illumination is structured in turn by the modulation. The line shaped illumination allows a confocal slit detection and, thus, once again an enhanced resolution. This method is also abbreviated to SLIM [spatial light interference microscopy].

An even higher increase in the resolution is attained, when the illumination radiation modulation is carried out at the illumination radiation and is so intensive that the fluorescence of the specimen achieves a saturation into the bright area of the structured illumination. Then the modulation on the specimen no longer has a sine distribution with respect to the fluorescence, but rather has an even higher harmonics beyond the optical limit frequency. This method is also abbreviated to saturated pattern excitation microscopy (SPEE).

SUMMARY OF THE INVENTION

The invention describes below a method and a device for achieving a microscopic resolution below the diffraction limit of the microscope as disclosed in the independent claims. Preferred further developments are the subject matter of the dependent claims.

FIG. 3 shows a microscope 1 that can carry out the standard microscopy method—that is, the microscopy method has a resolution that is diffraction limited—simultaneously with high resolution microscopy methods—that is, with microscopy methods that have a resolution that is increased beyond the diffraction limit. The microscope 1 is modular in structure, and it is described in a comprehensive expansion stage in order to illustrate the invention with greater clarity. However, a reduced design with fewer modules is also possible. Furthermore, the modular design is also not absolutely mandatory; a one piece or non-modular design is also possible. The microscope 1 of this example in FIG. 1 is constructed on the basis of a conventional laser scanning microscope and detects a specimen 2.

Said microscope has an objective lens 3, through which the radiation passes for all microscopy methods. The objective lens 3 images by means of a beam splitter 4, the specimen together with a tube lens 5 onto a CCD detector 6 that is an example of a generally optional two-dimensional detector. In this respect the microscope 1 has a conventional light microscope module 7, and the beam path from the specimen 2 through the objective lens 3 and the tube lens 5 to the CCD detector 6 corresponds to a conventional wide field detection beam path 8. The beam splitter 4 can be exchanged, as indicated by the double arrow in FIG. 1, in order to be able to switch between beam splitters with differing dichroic properties or achromatic beam splitters according to US 2008/0088920.

Also connected into the beam path to the objective lens 3 is a laser scanning module 9 having an LSM [laser scanning microscopy] illumination and detection beam path that is coupled into the beam path to the objective lens 3 by way of a switching mirror 11 that also has beam splitter functions. Hence, the beam path from the switching mirror 11 to the objective lens 3 through the beam splitter 4 is a beam path, in which the illumination beam path and the detection beam path are combined. This feature applies to both the laser scanning module 9 and also to the wide field detection beam path 8, since the illumination radiation that realizes the microscopy method together with the wide field detection beam path 8—that is, with the CCD detector 6—is also coupled in at the switching mirror 11, which will be explained in detail below.

The switching mirror 11 and the beam splitter 4 are combined into a beam splitter module 12, so that there is the possibility of exchanging the switching mirror 11 and the beam splitter 4 as a function of the application. This option is shown by the double arrows. Furthermore, the beam splitter module 12 has an emission filter 13, which lies in the wide field detection beam path 8 and suitably filters the spectral proportions, which can propagate through the wide field detection beam path 8. Of course, the emission filter 13 in the beam splitter module 12 can also be exchanged.

The laser scanning module 9 obtains the laser radiation that is necessary for the operation from a laser module 15 by way of an optical fiber 14.

BRIEF DESCRIPTION OF THE DRAWINGS

The invention will be described in connection with the annexed drawings, in which:

FIG. 1 is a schematic representation of fluorescence as known in the prior art.

FIG. 2 is a schematic representation of illumination path in prior art microscopy.

FIG. 3 shows a microscopic design according to the present invention.

FIG. 4 shows in schematic form the superimposition of the different microscopy images that are obtained by means of the combination microscope according to the invention.

DESCRIPTION OF THE EMBODIMENTS

Figure 5:
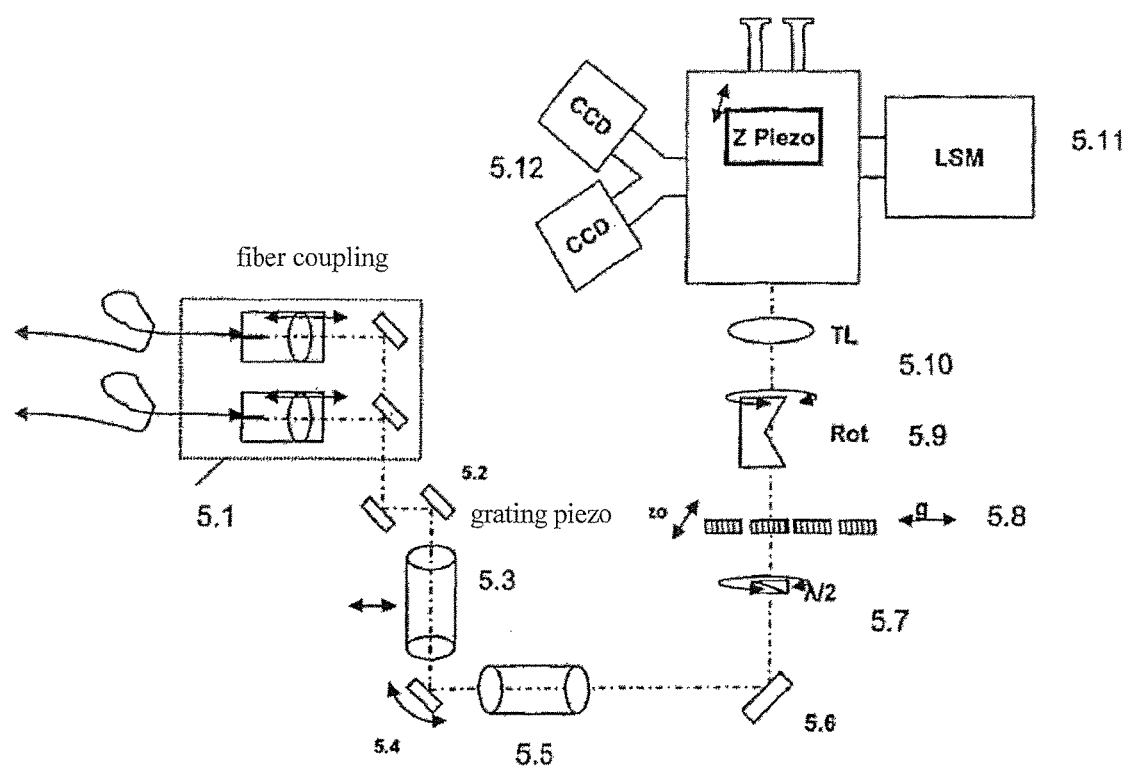
FIG. 5 shows an embodiment of an additional optical arrangement for the invention.

In the in FIG. 3, a collection illumination beam path 16, through which the illumination radiation passes for different microscopy methods, is coupled in at the beam splitter module 12—stated more precisely at the switching mirror 14. Different partial illumination beam paths of individual illumination modules are coupled into this collection illumination beam path 16. For example, a wide field illumination module 17 couples the wide field illumination radiation into the collection illumination beam path 16 by way of a switching mirror 18, with the result that the specimen 2 is wide field illuminated by way of a tube lens 27 and the objective lens 3. The wide field illumination module can have, for example, an HBO lamp. An additional illumination module that may be provided is the TIRF illumination module 19 that provides a TIRF illumination, when the switching mirror 18 is in a suitable position. For this purpose the TIRF illumination module 19 receives radiation from the laser module 15 by way of an optical fiber 20. The TIRF illumination module 19 has a mirror 21 that can be moved longitudinally. Owing to the longitudinal shift the illumination beam, which is emitted by the TIRF illumination module 19, is moved perpendicular to the main propagation direction of the emitted illumination beam, as a result of which the TIRF illumination impinges on the objective lens 3 at an adjustable angle to the optical axis of the objective lens 3.

This feature makes it easy to ensure the necessary angle of the total internal reflection at the cover glass. Of course, other means for effecting this angle adjustment are also suitable. The TIRF illumination module 19 can also operate as a wide field illumination source by adjusting the mirror 21 in such a way that the illumination beam impinges on the optical axis.

Furthermore, the illumination beam path of a manipulator module 22, which also receives radiation from the laser module 15 by way of an optical fiber (not identified in detail)

and guides a spot or line shaped beam distribution in a scanning manner over the specimen 2, is coupled to the collection illumination beam path. Thus, the manipulator module 22 corresponds more or less to the illumination module of a laser scanning microscope, and consequently the manipulator module 22 can also be operated combined with the detector of the laser scanning module 9 or the wide field detection by means of the CCD detector 6.

Furthermore, the collection illumination beam path 16 has a strip grating 23, which is provided as a radiation modulator and which lies in an intermediate image plane of the illumination beam path. The grating constant of this strip grating lies below the limit frequency that can be transmitted into the specimen 2 with the microscope 1. The grating 23 brings about a stripe-shaped modulation of the illumination radiation incident on it. The grating 23 can be shifted transversely to the optical axis of the collection illumination beam path 16 and can also be swiveled out of the beam path. For this purpose, there is a corresponding shift drive 24.

Furthermore, an image field rotator 25, which is rotated by a rotator drive 26, sits downstream of the grating in the illumination direction in the collection illumination beam path 16. The image field rotator can be, for example, an Abbe König prism.

The modules and the drives as well as the detectors of the microscope 1 are all connected to a control unit 28 by way of lines that are not identified in detail. This connection can take place, for example, by way of a data and control bus. The control unit 28 drives the microscope 1 into different operating modes.

The control unit 28 is designed to have the microscope 1 carry out standard microscopy—that is, wide field microscopy (WF), laser scanning microscopy (LSM) and also total internal reflection fluorescence microscopy (TIRF)—and to combine these three with high resolution microscopy methods, such as in the PAL-M, SIM, SLIM, SPEM, STED, RESOLFT described in the introductory part, and also to combine these with one another. The microscope 1 in FIG. 1 has in essence two modules that lend themselves well to laser scanner illumination—that is, the laser scanning module 9 as well as the manipulator module 22. Of course, other combinations are also possible. These modules are coupled onto the specimen 2 by way of the tube lenses and the objective lens 3. The manipulator module 22 contains only the excitation part of a laser scanning module—thus, without detection. As a result, the specimen can be illuminated spot by spot; and the illumination spot can be scanned over the specimen 2. Preferably the manipulator module 22 also has a switching unit—that is, a switching lens or cylindrical lens, with which a switch between a spot by spot and a line shaped illumination takes place. Then this line shaped illumination is advantageous, especially if the grating 23, which is located in an intermediate image of the collection illumination beam path 16, is swiveled in and lies perpendicular to the line of the line shaped illumination. Then the SLIM microscopy method can be easily implemented by means of the manipulator module 22.

As an alternative to the grating 23, a variably adjustable stripe modulator or a DMD can also be used to generate a structured illumination in the specimen 2. Then, of course, the shift drive 24 as well as the ability of the grating 23 to swivel in/out are no longer necessary.

The image field rotator 25 allows the structured illumination, which is generated by the grating 23 (or the elements replacing this grating), to rotate about the optical axis of the collection illumination beam path 16, so that the structured illumination lies at different angles in the specimen 2. As a result, SIM, SLIM or SPEM microscopy can be carried out with the microscope 1 by operating the manipulator module 22 or the wide field illumination module 17, in each case in combination with suitable adjustment of the grating 23 by means of the control unit 28. Then, of course, the switching mirror 18 has to be moved into the suitable position.

When the grating 23 is swiveled out, a standard wide field illumination by means of the wide field illumination module 17 or a standard TIRF illumination by means of the TIRF illumination module 19 can be effected.

In order to switch between the individual operating modes, the switching mirrors 18 and 11 as well as the beam splitter 4 are suitably adjusted. For this purpose, folding or swivel mirrors can be used in the implementation, with the result that a switch-over between the operating modes can be effected sequentially. As an alternative, dichroic mirrors, which enable a simultaneous operation of the different modules, are also possible.

The beam splitter 4 is designed preferably as a dichroic beam splitter having spectral properties that can be adjusted in such a way that the spectral proportions of the fluorescence emission of tagging molecules, which are to be detected with the help of the CCD detector 6, enter the wide field detection beam path 8, and the remaining spectral components are transmitted to the greatest possible extent. In order to increase the flexibility with respect of the usability of tagging molecules with different emission characteristics, several different beam splitters 4 and emission filters 13 are arranged in an exchangeable manner in the beam splitter module 12, for example, on a filter wheel.

FIG. 4 shows in schematic form the superimposition of the different microscopy images that are obtained by means of the combination microscope according to the invention. In this case the microscopy image 29 originates from a standard microscopy method, for example from normal fluorescence microscopy using the wide field illumination source 17 and the wide field detection. The microscopy image 30, on the other hand, originates from a high resolution method, for example a SIM or PAL microscopy. There are structures 31 in the microscopy image 29; the structures 32 are present in the high resolution microscopy image 30. At this point the control unit 28 superimposes the respective images into a total image in a superimposition procedure 33 that is symbolized by an arrow. The superimposition can take place in a two-dimensional manner, a three-dimensional manner and also over time for both variants in each case. FIG. 2 shows a two-dimensional representation by way of example. Furthermore, FIG. 2 shows in schematic form that a higher resolution microscopy image 30 is combined with a lower resolution microscopy image 29—that is, that the combination of two microscopy methods with different resolutions results in a total image. It is very clear from FIG. 2 that only with the aid of the lower resolution microscopy image 29 can a relationship between the high resolution details of the higher resolution microscopy image 30 be produced.

FIG. 5 shows an embodiment of an additional optical arrangement for the invention.

The illumination light is coupled in by means of a fiber coupling 5.1, which consists of optical fibers, collimation lenses and deflecting mirrors.

Deflecting mirrors 5.2 make it possible to reduce the image field in the TIRF mode onto a tiltable mirror 5.4 by way of a preferably adjustable telescope 5.3; and the TIRF angle of this tiltable mirror can be adjusted.

An additional telescope 5.5 and a deflecting mirror 5.6 as well as a rotatable lambda/half plate for the rotation of the polarization allow the collimated light to pass into the plane of the grating 5.8 that is intended for the structured illumination described above and is preferably exchangeable and finely shiftable perpendicular to the optical axis by means of a piezo drive, and a rotatable prism for image rotation 5.9, a tube lens 5.10 into a microscope (shown only in schematic form), which has a piezo drive for the Z adjustment. An LSM 5.11 beam path is coupled to the microscope in a way known from the prior art (see, for example, DE 19702753 A1). In this case two parallel CCD cameras 5.12 are arranged in the detection for wide field detection.

Once again it is very clear from FIG. 5 that it is possible to generate images, stored in a combination device for TIRF illumination and for structured (SIM) illumination, from both methods. Preferably the grating is swiveled out for TIRF illumination and then for detection.

When the grating is swiveled in, a high resolution wide field image can be determined from the illumination with one or more receivers 5.1 in a plurality of grating phases and then for calculation.

When the same objective lens is used, the image fields for the SIM acquisition and the TIRF acquisition are identical, so that a computational balancing of the images is easily possible. In the event of different objective lenses or other changes in the acquisition conditions, it is possible to take such measures that are known to the person skilled in the art in order to adapt the image field, for example, by a calibration of the objective lenses that are used and in order to make computational corrections of the image fields.

Therefore, the data acquisition is a temporal sequence of image that contains, on the one hand, all of the necessary images for SIM, as well as a TIRF image without grating in the beam path—that is, without structuring. The sequence of the acquisition is immaterial and offers only speed related advantages based on the hardware. If, for example, the changing of the illumination to TIRF is time consuming, then it makes sense to perform this movement only once—that is, to take the TIRF image at the beginning or the end of the image series. In other words, the thin TIRF plates in the vicinity of the object carriers can be structured "laterally" by the calculation.

It is also possible to generate SIM images in stacks by a Z adjustment. Then a TIRF acquisition takes place at the lower image of the stack (the bottommost layer of the object). What is meant by the bottommost layer in this case is the layer that lies in the vicinity of the cover glass. In a microscope that is different from an inverse microscope, it could also be the "uppermost" layer. Surprisingly after computational balancing by multiplication of the image data, the result for the bottommost layer is an image that exhibits high lateral resolution with respect to Z and also in the Y/Y direction.

Therefore, following the acquisition of data, there are, for example, for SIM 15 images (5 phases are the 5 phases 0 deg., 72 deg., 144 deg., etc.; 3 image directions by adjustment of 5.9) and an acquired TIRF image.

Figure 6:
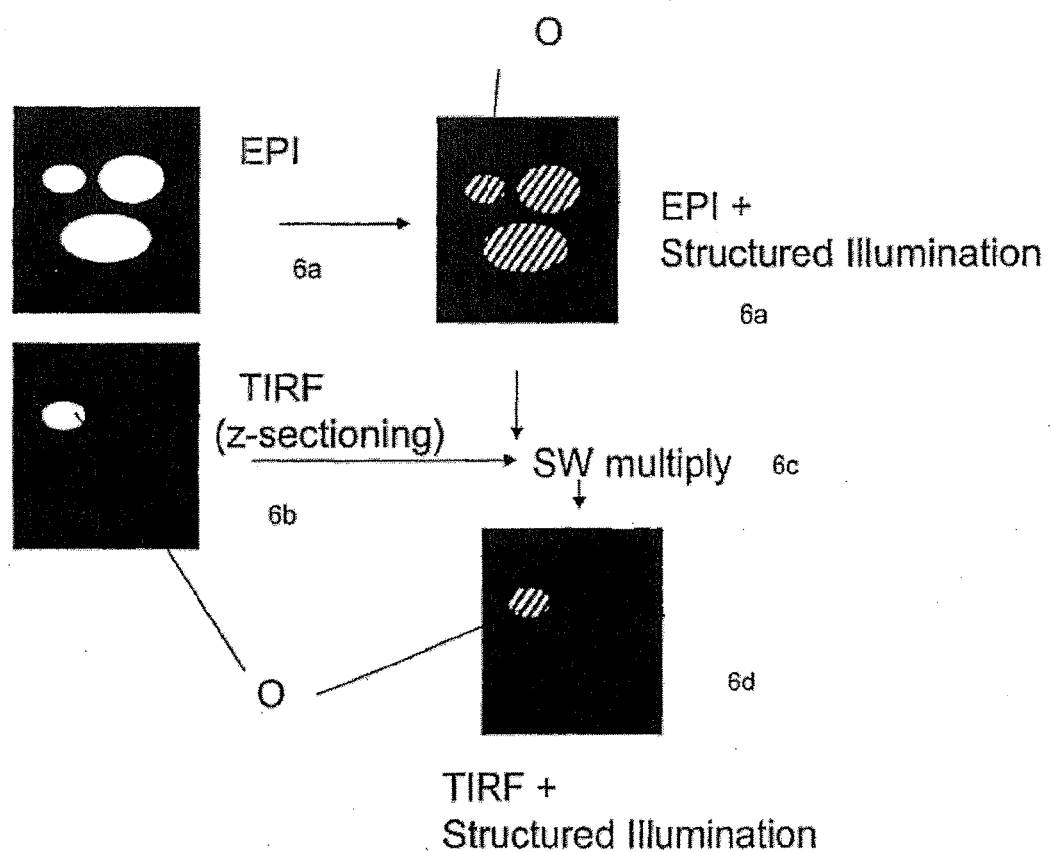
FIG. 6 shows the stored individual images for TIRF 6a and 6b for structured (SIM) illumination.

FIG. 6 shows the stored individual images for TIRF 6a and 6b for structured (SIM) illumination.

At this point they are linked together by computational procedures (preferably multiplied) in 6c, as a result of which an image 6d is calculated that also imparts to the image, acquired in the vicinity of the object carrier, a lateral structuring for an object O, which is present in both images.

Figure 7:
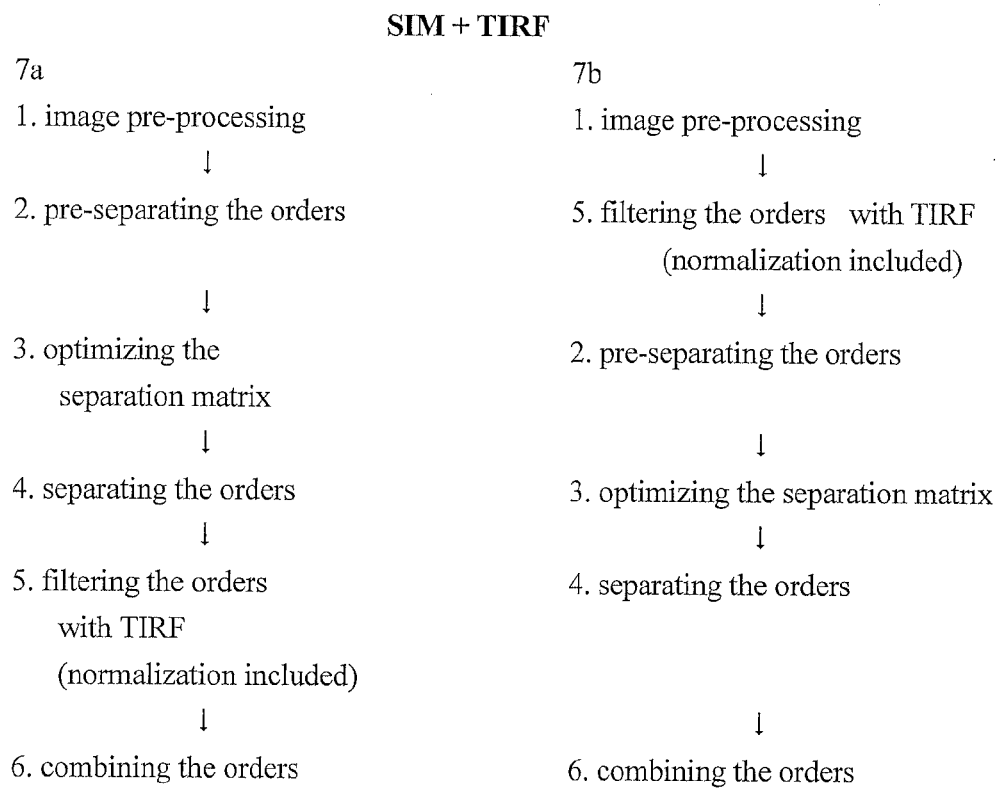
FIGS. 7a and 7b show possible sequences.

The actual linking of the images consists, as shown in FIG. 7, of a filter process of the SIM data with the TIRF image, which can be done by means of simple multiplication. The image shows two practical sequences of the computational balancing of the SIM data and positions, in which the combination with the TIRF image can occur.

The steps 1 to 4, 6 are all standard SIM balancing procedures; step 5 of the new step of the TIRF weighting that is introduced here.

The sequence is in detail as follows:

1. The 15 images are preprocessed in a way that is typical for SIM (for example, removal of background (optionally, by incorporation of an additional background image), scaling of the respective 5 phases to the same average intensities; the edges of the images are attenuated in order to suppress artifacts of the Fourier transformation).

2. The next step is one, in which the orders are then pre-separated in order to be actually separated after optimization of the separation matrix. What is meant by orders in this context is the Moiré patterns generated by the different diffraction orders of the grating. The linear combination of the Moiré patterns is observed in each individual image. The acquisition of different phase images makes it possible to obtain a linear equation system having a solution that is the separated contributions (orders). Details of the derivation can also be found in: "Doubling the lateral resolution of wide field fluorescence microscopy" by Gustafson, Agard, Sedat, SPIE, Vol. 3919 (2000), pp. 1605-7422.

In order to obtain relations (concentrations of fluorophores) in the image that have nothing to do with TIRF sectioning, a normalization should also be performed after the multiplication. This normalization corrects for the linear case—that is, takes the square root—, so that lateral intensity relations remain. That means that the intensity values that may be seen in TIRF and in SIM retain their original value after the weighting and are not squared.

FIGS. 7a and 7b show possible sequences.

It involves the steps (see also the description of the formulas and the reference to these steps):

1. image processing (for example, elimination of the background, application of a smoothing filter)
2. pre-separating the orders
3. optimizing the separation matrix
4. separating the orders
5. filtering the orders with TIRF, for example by multiplication preferably with subsequent normalization (for example, square root)
6. combining the orders (joint computational balancing and image display)

Then in FIG. 7a an acquisition and calculation of the individual orders of an image taken with structured illumination are performed and then balanced with the TIRF image. Then an image is calculated from the orders and stored (step 5). In FIG. 7b a TIRF acquisition is performed first; and thereafter the acquisition of the structured image and the calculation of the orders and computational balancing with the TIRF image and finally combination of the orders of the images.

With respect to the mathematical basis of the SIM method the following must be added (see also the cited literature):

Illumination pattern in the Fourier space:

$$I(k)=a_0\delta(k)+a_1[e^{-i\phi}\delta(k+k_g)+e^{-i\phi}\delta(k-k_g)]+a_2[e^{-i2\phi}\delta(k+2k_g)+e^{-i2\phi}\delta(k-2k_g)] \quad (1),$$

where $a_0$, $a_1$, and $a_2$ describe, as the amplitudes of the intensity of the illumination orders $k_g$, the grating vector. The grating vector $k_g=(x_k, y_k)$ contains the information about the grating frequency ("pixel size"/$|k_g|$) and the direction (a tan 2 $(y_k/x_k)$).

Imaging: I(k) is multiplied by the optical transfer function (OTF), $H_{ex}(k)$ $$I_{ex}(k)=H_{ex}(k)I(k) \quad (2)$$

$I_{ex}(k)$ is folded with the object S(k) in the Fourier space $$I_S(k)=\int I_{ex}(k')S(k-k')dk'=\int H_{ex}(k')I(k')S(k-k')dk' \quad (3)$$

$I_S$ (k) is multiplied with the emissions OTF, $H_{em}$ (k)

$$I_{em}(k)=H_{em}(k)I_S(k)=H_{em}(k)\int H_{ex}(k')I(k')S(k-k')dk' \quad (4)$$

Inserting (1) into (4) yields:

$$I_{em}(k)=a_0 \hat{D}_0(k)+a_1[e^{i\phi}\hat{D}_{-1}(k)+e^{i\phi}\hat{D}_1(k)]+a_2[e^{i2\phi}\hat{D}_{-2}(k)+e^{i2\phi}\hat{D}_2(k)] \quad (5)$$

with the orders:

$$\hat{D}_x(k)=H_{em}(k)H_{ex}(xk_g)S(k-xk_g) \quad (6)$$

Inserting the order intensities $a_0$, $a_1$, and $a_2$ into $D_x(k)$ yields:

$$I_{em}(k)=D_0(k)+e^{i\phi}D_{-1}(k)+e^{i\phi}D_1(k)+e^{i2\phi}D_{-2}(k)+e^{i2\phi}D_2(k) \quad (7)$$

Separating the orders: In order to separate by five orders, $D_0(k)$, $D_{-1}(k)$, $D_1(k)$, $D_{-2}(k)$, and $D_2(k)$, one needs at least five images ($N_P=5$) acquired with different phases, $n=1, \ldots, N_p$:

$$I^n_{em}(k)=D_0(k)+e^{i\phi n}D_{-1}(k)+e^{i\phi n}D_1(k)+e^{i2\phi n}D_{-2}(k)+e^{i2\phi n}D_2(k), n=1, \ldots, N_p \quad (8)$$

The set (8) can be described in the matrix form as follows:

$$I=AD' \quad (9)$$

where $$I=\{I^n_{em}(k)\}_{n=1,\ldots,Np},$$

$$A=\{1, e^{-i\phi n}, e^{i\phi n}, e^{-i2\phi n}, e^{i2\phi n}\}_{n=1,\ldots Np},$$

$$D=\{D_0(k), D_{-1}(k), D_1(k), D_{-2}(k), D_2(k)\} \quad (10)$$

Note that the phases are selected in such a way that the linear equation system (8) consists of linearly independent equations. Then the set (8) can be solved for $D_0(k)$, $D_{-1}(k)$, $D_1(k)$, $D_{-2}(k)$, and $D_2(k)$ as follows.

Optimizing the separation matrix: Separating the orders according to the equations (8) assumes that the phases $D_n$ are known accurately enough.

In optimizing the separation matrix: Separating the orders according to the equation (8) assumes that the phases $D_n$ are known accurately enough. However, in experiments these values can deviate sometimes considerably from the assumptions; hence, the grating frequency and the phases should be determined together with the orders from the data. Therefore, the pre-separation is done with the assumptions for the phases (pre-separation of the orders according to step 2 in FIG. 7) according to the equation system (8).

Then these pre-separated orders are used to optimize the separation matrix A (optimization of the separation matrix, step 3 in FIG. 7) by minimizing the cross correlation between the pre-separated orders. Then in the final step the orders are separated with this matrix A (step 4 in FIG. 7).

Then at this point the individual orders can be filtered with the TIRF image by multiplication (filtering the orders with TIRF step 5 in FIG. 7). Normalizing by taking the square root achieves the relative intensities in the image, because the intensities that can be seen with the same brightness in the TIRF and the wide field image retain the identical brightness value; others that cannot be seen as well in the TIRF are, however, shown darker, so that the desired Z sectioning takes place.

Then the high resolution image is assembled in the same way as described by Gustaffson et al., by combining the orders (shift in the frequency space and summing of the orders with weighting of the OTF) (combining the orders, step 6 in FIG. 7).

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. Method for generating a microscope image, comprising
   (a) illuminating a specimen via a microscope objective lens by means of a total internal reflection fluorescence (TIRF) method and detecting specimen light to generate a first image of at least one specimen area,
   (b) subsequent or prior to generating said first image of said at least one specimen area by illuminating the specimen by means of the TIRF method, illuminating said specimen of said at least one specimen area in a structured way in different shift positions of the structure, and detecting specimen light when said specimen is illuminated at said at least one specimen area by structured light to generate multiple second images of said at least one specimen area, said second images being different from said first image,
   (c) separating orders of said secondary images,
   (d) filtering said orders of said secondary images by means of said first image by multiplication, and
   (e) combining said orders of said filtered secondary images by joint computation and displaying the combination.

2. Microscope for carrying out the method claimed in claim 1, further comprising
   a first illumination means for generating a TIRF illumination and providing a second illumination means for generating a structured illumination;
   detection means for detecting a first image of said specimen under said TIRF illumination and second images of said specimen under said structured illumination;
   means for storing the first and second images;
   and means for computationally combining said images, in particular by multiplication.

3. Microscope for carrying out the method as claimed in claim 1, further comprising
   illumination means, detection means and an imaging and illumination beam path which contains a microscope objective lens,
   a first illumination means for generating a TIRF illumination and a second subsequent illumination means for generating a structured illumination,
   detection means for detecting a TIRF image and images of the specimen that is illuminated in a structured manner;
   providing means for storing said TIRF image and an image of the specimen that is calculated from said images under said structured illumination in different shift positions of the structure; and
   providing means for computationally combining said images and storing the results.

4. Microscope according to claim 2 further comprising means for displaying the image as the result of computational combination.

5. The method according to claim 1, wherein the step of the first and second images according to paragraphs a) and b) being combined are combined by being multiplied.

6. Method for generating a microscope image, comprising
  a) illuminating a specimen via a microscope objective lens by means of a total internal reflection fluorescence (TIRF) method and detecting specimen light to generate a first image of at least one specimen area,
  b) subsequent or prior to generating said first image of said at least one specimen area by illuminating the specimen by means of the TIRF method, illuminating said specimen of said at least one specimen area in a structured way in different shift positions of the structure and detecting specimen light when said specimen is illuminated at said at least one specimen area by structured light to generate multiple second images of said at least one specimen area, said second images being different from said first image,
  wherein the first and second images, generated according to paragraphs a) and b), are combined, and
  c) storing results in order to generate a new specimen image.

7. Method for generating an image of a specimen, according to claim 6, by microscopy methods that provide different spatial resolutions, wherein at least two of the following microscopy methods are combined:
  exciting said specimen to luminesce by structured line or wide field illumination in a first microscopy method; rotating and shifting said structuring several times for each rotational position; wherein at least three rotational positions and for each rotational position at least three shift positions are provided; imaging in each case the luminescent specimen onto a two-dimensional detector with a predetermined optical resolution; and from the resulting images a first microscopy image with a spatial resolution that is increased beyond the predetermined optical resolution is generated by a computational processing comprising a Fourier analysis;
  and in a second microscopy method the specimen is to be illuminated in such a tilted manner through the objective lens by way of a TIRE illumination module that total internal reflection takes place in a specimen arranged on the cover glass; and this total internal reflection is detected in a spatially resolving manner, and a second microscopy image is generated,
  wherein the first and second microscopy images are combined pixel by pixel by a computational procedure, preferably by multiplication.

8. Method, as claimed in claim 7, wherein the result of the computational combination is shown in the form of an image.

9. The method according to claim 6, wherein the step of the first and second images according to paragraphs a) and b) being combined are combined by being multiplied.

* * * * *

UNITED STATES PATENT AND TRADEMARK OFFICE
CERTIFICATE OF CORRECTION

| | |
|---|---|
| PATENT NO. | : 9,588,045 B2 |
| APPLICATION NO. | : 13/499328 |
| DATED | : March 7, 2017 |
| INVENTOR(S) | : Ingo Kleppe and Yauheni Novikau |

Page 1 of 1

It is certified that error appears in the above-identified patent and that said Letters Patent is hereby corrected as shown below:

In the Specification

Column 4, Line 32: now reads: "In the in FIG.3, a collection illumination beam path 16,"
Should read: --In FIG. 3, a collection illumination beam path 16,--

Column 9, Line 12: now reads: " $I_{em}(k) = a_0 D\hat{\,}_0(k) + a_1 \lfloor e^{i\varphi} D\hat{\,}_{-1}(k) + e^{i\varphi} D\hat{\,}_1(k) \rfloor + a_2 \lfloor e^{2i\varphi} D\hat{\,}_{-2}$ "
Should read: -- $I_{em}(k) = a_0 D\hat{\,}_0(k) + a_1 \lfloor e^{i\varphi} D\hat{\,}_{-1}(k) + e^{i\varphi} D\hat{\,}_1(k) \rfloor + a_2 \lfloor e^{i2\varphi} D\hat{\,}_{-2}$ --

In the Claims

Column 12, Line 15: now reads: "tive lens by way of a TIRE illumination module that"
Should read: --tive lens by way of a TIRF illumination module that--

Signed and Sealed this
Twenty-ninth Day of August, 2017

Joseph Matal
*Performing the Functions and Duties of the
Under Secretary of Commerce for Intellectual Property and
Director of the United States Patent and Trademark Office*